United States Patent
Fetzner

(10) Patent No.: US 10,094,771 B2
(45) Date of Patent: Oct. 9, 2018

(54) DEVICE AND METHOD FOR DETERMINING THE CONCENTRATION OF AT LEAST ONE GAS IN A SAMPLE GAS STREAM BY MEANS OF INFRARED ABSORPTION SPECTROSCOPY

(71) Applicant: AVL EMISSION TEST SYSTEMS GMBH, Neuss (DE)

(72) Inventor: Stephan Fetzner, Forst (DE)

(73) Assignee: AVL EMISSION TEST SYSTEMS GMBH, Neuss (DE)

( * ) Notice: Subject to any disclaimer, the term of this patent is extended or adjusted under 35 U.S.C. 154(b) by 1 day.

(21) Appl. No.: 15/115,693

(22) PCT Filed: Jan. 15, 2015

(86) PCT No.: PCT/EP2015/050640
§ 371 (c)(1),
(2) Date: Aug. 1, 2016

(87) PCT Pub. No.: WO2015/121017
PCT Pub. Date: Aug. 20, 2015

(65) Prior Publication Data
US 2017/0010208 A1    Jan. 12, 2017

(30) Foreign Application Priority Data

Feb. 14, 2014 (DE) .................... 10 2014 101 915

(51) Int. Cl.
*G01N 21/35* (2014.01)
*F04F 5/50* (2006.01)
(Continued)

(52) U.S. Cl.
CPC ........... *G01N 21/3504* (2013.01); *F04F 5/50* (2013.01); *G01N 21/05* (2013.01); *G01N 21/39* (2013.01);
(Continued)

(58) Field of Classification Search
CPC .................. G01N 21/3504; F04F 5/50
See application file for complete search history.

(56) References Cited

U.S. PATENT DOCUMENTS 3,593,023 A * 7/1971 Dodson ............... G01M 15/108
250/343
4,762,467 A * 8/1988 Ackermann ............ F04F 5/52
417/185

(Continued)

FOREIGN PATENT DOCUMENTS

DE    10 2006 005 901 B3    8/2007
EP    2 657 685 A1    10/2013
(Continued)

*Primary Examiner* — Casey Bryant
(74) *Attorney, Agent, or Firm* — Norman B. Thot

(57) ABSTRACT

A device for determining a concentration of at least one gas in a sample gas flow by infrared absorption spectroscopy. The device includes an infrared radiation source which emits a radiation which is conducted through an analysis cell, a feed line, the sample gas flow which is conducted into and out of the analysis cell via the feed line, a detector which measures an absorption spectrum arising in the analysis cell, a suction jet pump which includes a propellant gas connection, and a propellant gas line which extends to the propellant gas connection of the suction jet pump. The suction jet pump is arranged downstream of the analysis cell and feeds the sample gas flow through the analysis cell via the feed line. The propellant gas line includes a regulating valve which regulates a propellant pressure in the propellant gas line.

12 Claims, 2 Drawing Sheets

(51) Int. Cl.
    *G01N 21/3504*    (2014.01)
    *G01N 21/05*       (2006.01)
    *G01N 21/39*       (2006.01)
    *G01L 19/00*       (2006.01)

(52) U.S. Cl.
    CPC .... *G01L 19/0092* (2013.01); *G01N 2021/399* (2013.01)

(56) References Cited

U.S. PATENT DOCUMENTS

| | | |
|---|---|---|
| 5,147,426 A | 9/1992 | Koike et al. |
| 5,271,900 A * | 12/1993 | Morita ............... G01N 21/3504 |
| | | 250/356.1 |
| 6,058,789 A | 5/2000 | Kohsaka et al. |
| 2007/0034792 A1 | 2/2007 | Zhang et al. |
| 2010/0284006 A1 | 11/2010 | Socha et al. |
| 2011/0285998 A1 | 11/2011 | Hara et al. |
| 2013/0250301 A1 * | 9/2013 | Feitisch ............. G01N 21/3504 |
| | | 356/409 |
| 2014/0002823 A1 * | 1/2014 | Nakatani ........... G01N 21/3504 |
| | | 356/439 |

FOREIGN PATENT DOCUMENTS

| | | |
|---|---|---|
| JP | 49-44154 Y | 12/1974 |
| JP | 62-121997 A | 6/1987 |
| JP | 63-121958 U | 8/1988 |
| JP | 2012-2799 A | 1/2012 |
| JP | 2013-29395 A | 2/2013 |

* cited by examiner

DEVICE AND METHOD FOR DETERMINING THE CONCENTRATION OF AT LEAST ONE GAS IN A SAMPLE GAS STREAM BY MEANS OF INFRARED ABSORPTION SPECTROSCOPY

CROSS REFERENCE TO PRIOR APPLICATIONS

This application is a U.S. National Phase application under 35 U.S.C. § 371 of International Application No. PCT/EP2015/050640, filed on Jan. 15, 2015 and which claims benefit to German Patent Application No. 10 2014 101 915.6, filed on Feb. 14, 2014. The International Application was published in German on Aug. 20, 2015 as WO 2015/121017 A1 under PCT Article 21(2).

FIELD

The present invention relates to a device for determining the concentration of at least one gas in a sample gas flow by infrared absorption spectroscopy, the device comprising an infrared radiation source the radiation of which is adapted to be directed through an analysis cell, a sample gas flow which is adapted to be directed into the analysis cell and out of the analysis cell by a feed line, a detector via which an absorption spectrum arising in the analysis cell is adapted to be measured, and a suction jet pump which is arranged downstream of the analysis cell and via which measurement gas is adapted to be conveyed through the analysis cell and the feed line. The present invention also relates to a method for determining the concentration of at least one gas in a sample gas flow by infrared absorption spectroscopy with the aid of the device, wherein a radiation of an infrared radiation source is directed into an analysis cell through which a sample gas flow flows that is sucked in by a suction jet pump via a feed line, whereupon an absorption spectrum of the radiation exiting the analysis cell is determined by a detector, and the concentration of a gas in the sample gas flow is calculated on the basis of the absorption spectrum in a computing unit.

BACKGROUND

Infrared spectroscopy for determining the concentration of individual gas components has previously been described. The most common methods relate to the Fourier transform infrared spectrometer or the non-dispersive infrared spectrometer. With the development of compact high-power semiconductor lasers, gas analyzers based on the laser spectroscopy have been established to an increasing extent. New laser types, such as quantum cascade lasers, have revolutionized laser spectroscopy in the medium infrared range.

All of the above analyzing methods rely on specific frequency ranges being absorbed during irradiation of a sample gas with infrared beams. The infrared radiation lies in the range of the oscillation level of the molecular bonds which are induced to oscillate by the absorption. A prerequisite therefor is a dipole moment which is already present or which is generated in the molecule. The different oscillation states cause absorption losses of the infrared radiation of different optical frequencies. The spectrum in the transmission thus contains individual absorption lines characteristic of the gas so that the sample gas can be examined for the presence of specific molecules, and their concentration in the sample gas can be determined.

A quantum cascade laser can in particular determine pollutant molecules present in the exhaust gas of an internal combustion engines, such as dinitrogen monoxide, nitrogen monoxide, nitrogen dioxide, carbon dioxide, carbon monoxide, and ammonia, and their concentration.

Common laser-spectroscopic systems comprise a laser as a radiation source, the radiation of which is conducted into a gas cell via an optical path. The beam is repeatedly reflected in the gas cell via a suitable mirror configuration. A sample gas flow is at the same time introduced into the gas cell, wherein the radiation of the laser penetrates the sample gas flow and excites the molecules corresponding to the optical frequency. Energy of the respective frequency is absorbed due to this excitation, and the intensity of the transmitted beam decreases at this location in the spectrum. The absorption itself is not exactly defined, but is subject to broadening due to temperature and pressure changes. The beam having its spectrum changed in this manner exits the measuring cell and impinges upon a detector via which the changed frequency band is evaluated, thus allowing the presence of specific substances and their concentration to be determined. The sample gas flow is usually fed via a downstream vacuum pump.

When the concentration is determined, the absorption characteristic in the spectrum is evaluated and/or analyzed. This characteristic is generally referred to as the line spectrum of the absorbing gases. It has turned out, however, that the line shape in this spectrum depends on pressure and temperature. For the purpose of evaluation, these parameters must therefore either be kept constant or must be continuously metrologically detected and offset. The gas is therefore conditioned and the pressure and the temperature kept constant in order to increase measuring accuracy.

It has also turned out that in particular during the measurement of hot and wet gases, such as exhaust gases of internal combustion engines, condensate formation in the analysis cell must in any case be prevented since the condensate leads to a considerable falsification of the measuring results; the measuring temperatures must therefore frequently be increased. It has also turned out that cross sensitivities can be avoided with decreasing pressure since the absorption spectrum at a negative pressure becomes very narrow and high, whereby the spectra of the individual components no longer overlap each other. The analysis cells are therefore operated at a negative pressure which amounts, for example, to approximately 200 hPa absolute pressure.

It is therefore common practice to perform a feeding of the measurement gas via vacuum pumps. In the case of analyzers having quantum cascade lasers as a radiation source, this is usually performed by a membrane pump or a rotary vane pump.

These pumps are, however, disadvantageous in that they generate pressure bursts which result in pulsations in the feed line, which, again, has a negative effect on the quality of the measuring results if these pulsations are not corrected using additional components. Membrane pumps can also normally only be operated at an ambient temperature of up to 40° C. and are further constrained with regard to the temperature of the feed gas and/or high costs are incurred when a higher temperature resistance is required. Rotary vane pumps have a relatively high weight which makes them difficult to integrate into the housing of an analyzer. Both pump types also require regular maintenance and suffer from increased wear.

DE 10 2006 05 901 therefore describes an analyzer where the feeding of the gas is performed by a suction jet pump which is largely maintenance-free since it does not comprise any movable parts. The regulation of the feed pressure is effected via regulating valves arranged in the feed line.

The disadvantage of such a regulation is an increased propellant gas consumption since feeding must be carried out against the resistance of the throttle in the feed line so that a high propellant gas pressure always exists.

SUMMARY

An aspect of the present invention is to provide a device and a method for determining the concentration of at least one gas in a sample gas flow using infrared absorption spectroscopy wherein the measuring results are further improved compared with conventional designs by minimizing temperature fluctuations in the analysis cell. An additional aspect of the present invention is to provide a device which has a simple a setup and which requires little maintenance. Another aspect of the present invention is to provide a device where the consumption of required propellant gas and thus the operating costs incurred are kept as low as possible.

In an embodiment, the present invention provides a device for determining a concentration of at least one gas in a sample gas flow by infrared absorption spectroscopy. The device includes an infrared radiation source configured to emit a radiation which is conducted through an analysis cell, a feed line, the sample gas flow which is configured to be conducted into and out of the analysis cell via the feed line, a detector configured to measure an absorption spectrum arising in the analysis cell, a suction jet pump comprising a propellant gas connection, and a propellant gas line extending to the propellant gas connection of the suction jet pump. The suction jet pump is arranged downstream of the analysis cell and is configured to feed the sample gas flow through the analysis cell via the feed line. The propellant gas line comprises a regulating valve which is configured to regulate a propellant pressure in the propellant gas line.

BRIEF DESCRIPTION OF THE DRAWINGS

The present invention is described in greater detail below on the basis of embodiments and of the drawings in which.

DETAILED DESCRIPTION

Figure 1:
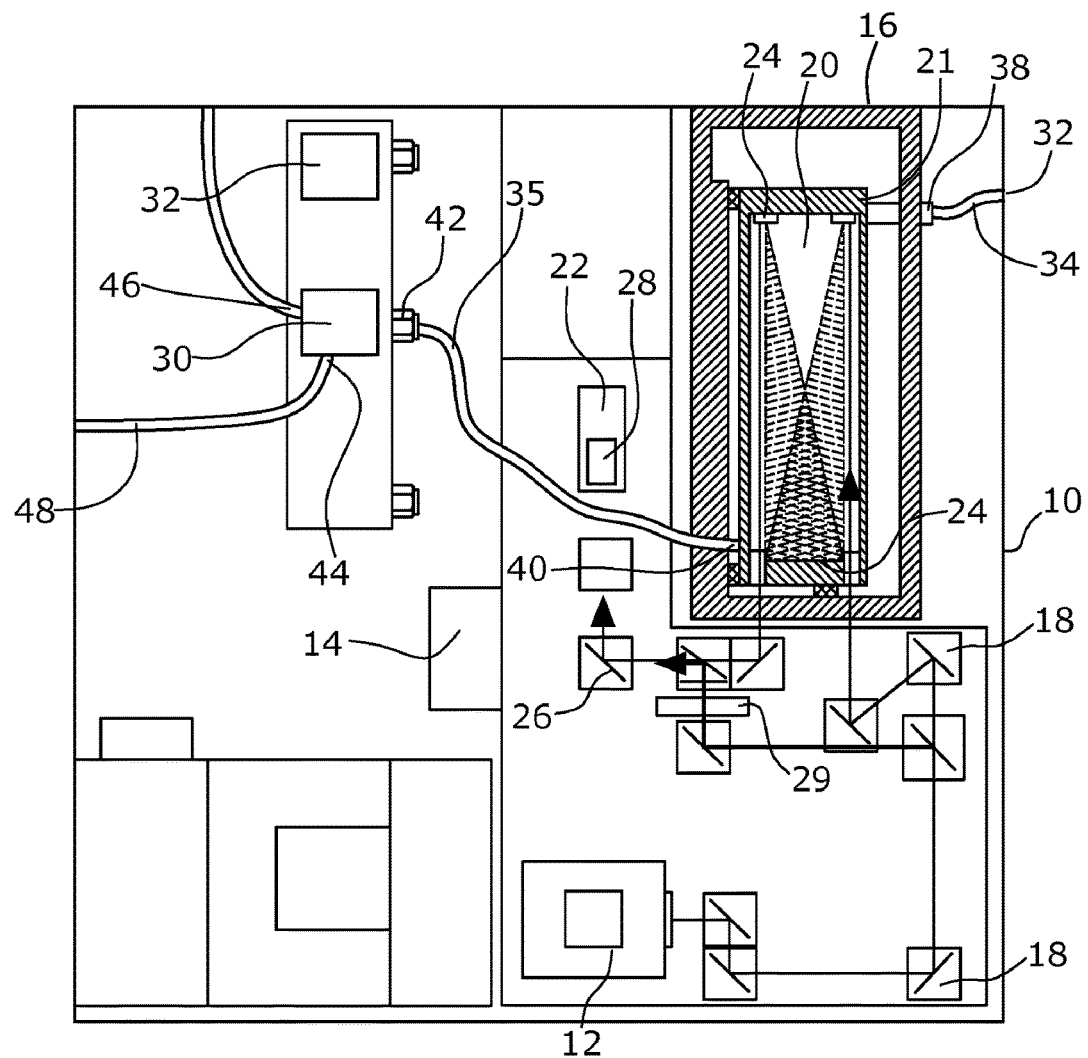
FIG. 1 shows a schematic top view of a device according to the present invention for determining the concentration of a gas in a sample gas flow.

Due to the fact that a regulating valve is arranged in a propellant gas line extending to a propellant gas connection of the suction jet pump via which the pressure in the propellant gas line is adapted to be adjusted, the pressure in the analysis cell is adjusted at the nozzle by changing the propellant gradient of the propellant gas. With regard to the method, this means that the propellant pressure in the propellant gas line and the propelling nozzle of the suction jet pump is regulated as a direct function of the feed pressure in the analysis cell or the feed line. The feed gas therefore does no need to be fed against a resistance, whereby the compressed air consumption is decreased since only that amount of compressed air is withdrawn that is required to generate the necessary pressure gradient.

In an embodiment of the present invention, the regulating valve can, for example, be a proportional valve which regulates the propellant pressure in the propellant gas line as a direct function of the feed pressure in the feed line downstream of the analysis cell or of the pressure in the analysis cell. This means that a higher propellant pressure is generated in the propellant gas line at a decreasing negative pressure in the feed line. No additional components or measuring equipment are required in such an embodiment. A steady state occurs at unchanged boundary conditions after a single calibration process. Additional measurements are not required since the proportional regulation immediately responds to a change of the pressure in the feed line by correspondingly changing the pressure in the propellant gas line, which results in a desired pressure change to the nominal pressure in the feed line.

In an embodiment of the present invention, the proportional valve can, for example, be a pneumatic valve comprising a control chamber which is fluidically connected with the feed line. The feed pressure in the feed line is accordingly directed into the control chamber of the proportional valve in the propellant gas line. In a corresponding configuration of the valve, an increase in the absolute pressure in the feed line may result in the regulating valve further opening the propellant gas line, for example, so that the negative pressure thus produced at the suction jet pump increases, whereby the absolute pressure in the feed line drops again and/or the negative pressure increases. Additional components for measurement and regulation are not required.

It can also be advantageous to arrange a pressure sensor downstream of the analysis cell in the feed line or in the analysis cell. Such a sensor may either be used to directly regulate a different regulating valve or to monitor or calibrate the proportional valve. Such an arrangement increases the reliability of the measurements and avoids errors.

In an embodiment of the present invention, the pressure sensor can, for example, be connected with a control unit of the regulating valve which regulates the position of the regulating valve as a function of the measured values of the pressure sensor. The feed pressure in the feed line is thus measured and the measured values are thus supplied to a control unit of a regulating valve arranged in the propellant gas line, wherein the regulating valve is controlled as a function of these pressure values. The pressure in the feed line can be regulated to any desired value in such an embodiment, and accordingly, an optimized pressure can be adjusted depending on the sample gas used. A very precise regulation is also possible which is completely independent of all boundary conditions.

In an embodiment of the present invention, the device can, for example, comprise a sample gas connection and a reference or purge gas connection which are optionally connectable with the feed line upstream of the analysis cell. In such an embodiment, a single suction jet pump can be used both to feed a reference gas flow and to feed the sample gas flow so that fewer components are required.

In an embodiment of the present invention, a branch can, for example, be defined in the feed line, in which branch a switch valve is arranged via which the feed line is optionally connectable with the sample gas connection or the reference or purge gas connection. A single valve can thus perform the switching between the two connections, whereby the number of components is again minimized and costs are thus saved.

It can also be advantageous when a nozzle is arranged in the feed line upstream of the analysis cell. This nozzle serves to limit a maximum volume flow.

In an embodiment of the present invention, the infrared radiation source can, for example, be a quantum cascade laser with the aid of which particularly accurate measurements of substances, such as oxides of nitrogen or ammonia, are possible.

A device and a method for determining the concentration of a gas in a sample gas flow by infrared absorption spectroscopy are thus provided via which the concentration and presence of a gas can be determined with high accuracy and reproducibility by reliably avoiding pressure fluctuations and pulsations. The setup is simple and requires little maintenance.

An exemplary embodiment of a device according to the present invention to determine the concentration of at least one gas in a sample gas flow by infrared absorption spectroscopy is illustrated in the drawings on the basis of a quantum cascade laser and is hereinafter described in conjunction with the method according to the present invention. The operating costs are low due to the reduction of the propellant gas consumption.

The device according to the present invention for determining the concentration of at least one gas in a sample gas flow by infrared absorption spectroscopy is configured as a quantum cascade laser absorption spectrometer in the present exemplary embodiment. The latter includes a housing 10 in which a quantum cascade laser 12 made up of semiconductor layers is arranged as an infrared radiation source, which can be operated either continuously or in a pulsed manner and in particular emits radiation in the medium infrared range. It is controlled via a current driver 14 and is cooled by a Peltier element (not illustrated).

The beam of the laser 12 is conducted into a chamber 20 of an analysis cell 16 via a plurality of mirrors 18 or is alternatively directly conducted to a detector 22 via the mirrors 18, which detector 22 may be an MCT (mercury cadmium telluride) detector, for example, that is in particular suitable for the photovoltaic detection in the medium infrared range and where an incident light quantum is directly converted into a measurable photocurrent. In chamber 20, this beam is repeatedly reflected at object or field mirrors 24, thus penetrating a sample gas which has been fed into the chamber 20. In specific frequency ranges of the emitted light band, this leads to absorption of the beam, which is characteristic of the presence and concentration of specific molecules. After the beam has been repeatedly reflected at the object or field mirrors 24, the beam exits the analysis cell 16 and is again supplied to the detector 22 via subsequent mirrors 26.

The optical frequency band measured by the detector 22 comprises gaps produced by the absorbed radiation, the size and the depth of the gaps being a measure of the concentration of the gas absorbing this frequency range. The corresponding conversion is performed in a conventional manner by a computing unit 28 with the aid of the Lambert-Beer law. The emitted wavelength of the laser 12 can be adjusted so that the absorption range of a specific absorption line of the gas component can be selectively swept, whereby cross sensitivities to other gas components are avoided. Gaps in the wavelength range of approximately 10 μm thus occur, for example, in the presence of ammonia.

It must be taken into account, however, that a reliable measurement is only possible in the case of a proper tuning between the path length of the beam and the expected concentration of the molecule to be measured in the sample gas flow so that either an undiluted or a diluted sample gas flow must be used.

It is in particular required that the measuring conditions be kept constant. Care must above all be taken that, besides a constant temperature, that the pressure in the analysis cell 16 is kept constant and that no pressure fluctuations occur during the measurement, if possible.

This is provided according to the present invention by feeding the sample gas flow by a suction jet pump 30 which sucks the sample gas flow into the chamber 20. For this purpose, the device comprises a sample gas connection 32 which is connected with an exhaust gas source, for example. The exhaust gas which is either undiluted or diluted by a know substance in a fixed ratio travels to a first part of a feed line 34. The first part of the feed line 34 extends to an inlet 38 of the analysis cell 16 and thus into the chamber 20 of the analysis cell 16 via a nozzle 36 by which a maximum volume flow of 1 l/min is, for example, determined. The sample gas flow again exits the chamber 20 via an outlet 40 which is connected with a second portion of the feed line 35. The end of this second portion of the feed line 35 is connected with a suction connection 42 of the suction jet pump 30, as is shown in FIG. 2.

Besides suction connection 42, suction jet pump 30 comprises a propellant gas connection 44 and an outlet 46. The propellant gas connection 44 is connected with a compressed air system 50 via a propellant gas line 48, which compressed air system 50 provides compressed air at a pressure, for example, of 7 bars. Alternatively, compressed air vessels may of course be used. The propellant gas enters the suction jet pump 30 via the propellant gas connection 44 at a correspondingly high velocity and passes through a propelling nozzle 52 which is frequently configured as a de Laval nozzle to maximize the velocity of the propellant gas so that a high dynamic pressure is produced at the outlet of the propelling nozzle 52. Due to this discharge from the propelling nozzle 52, a pulse transmission from the propellant gas to the sample gas occurs, due to friction and turbulences, in the downstream mixing chamber 54 where the suction connection 42 of the second part of the feed line 35 ends, namely, in the boundary layer between the rapid propellant gas and the sample gas, the sample gas being entrained by the propellant gas. In the mixing chamber 54, the propellant gas is relieved and is mixed with the sample gas flow so that the jet is decelerated. The high dynamic pressure is converted into a static pressure. The sample gas flow is accelerated by the propellant gas flow in the mixing chamber 54. A negative pressure is produced at the suction connection via which the sample gas is continued to be conveyed. Downstream of the mixing chamber 54, the suction jet pump 30 comprises a diffuser 56 which enhances the suction effect. The mixture of sample gas flow and propellant agent flow subsequently exits the suction jet pump 30 via the outlet 46. This gas mixture is then discharged from the device.

According to the present invention, the suction effect and thus the desired value of the negative pressure at the suction connection 42, which in the present case is to amount to approximately 200 hPa, is regulated in that the velocity of the propellant gas and thus the propellant pressure acting upon the sample gas flow are adjusted by throttling the propellant gas line 48. This is effected by a regulating valve 60 arranged in the propellant gas line 48, which regulating valve 60 is configured as a proportional valve in the exemplary embodiment. A proportional valve is an electropneumatic valve, the position of which depends on the current feed to a coil 62 of the electromagnet and on a pressure prevailing in a control chamber 64. The control chamber 64 is connected with the second part of the feed line 35 downstream of the analysis cell 16 so that the pressure of the propellant gas flow is a direct function of the pressure of the sample gas flow in the second part of the feed line 35. If a desired pressure value of 200 hPa is adjusted in the second part of the feed line 35, the configuration of the regulating valve 60 allows a selection of the current fed to the valve so that, at a lower absolute pressure in the second part of the feed line 35, the regulating valve 60 further closes the free cross-section so that the propellant pressure becomes lower and thus the pressure in the second part of the feed line 35 increases, and vice versa. For this purpose, the regulating valve 60 must be calibrated accordingly so that the state of the desired pressure in the second part of the feed line 35 always occurs as the steady state.

Figure 2:
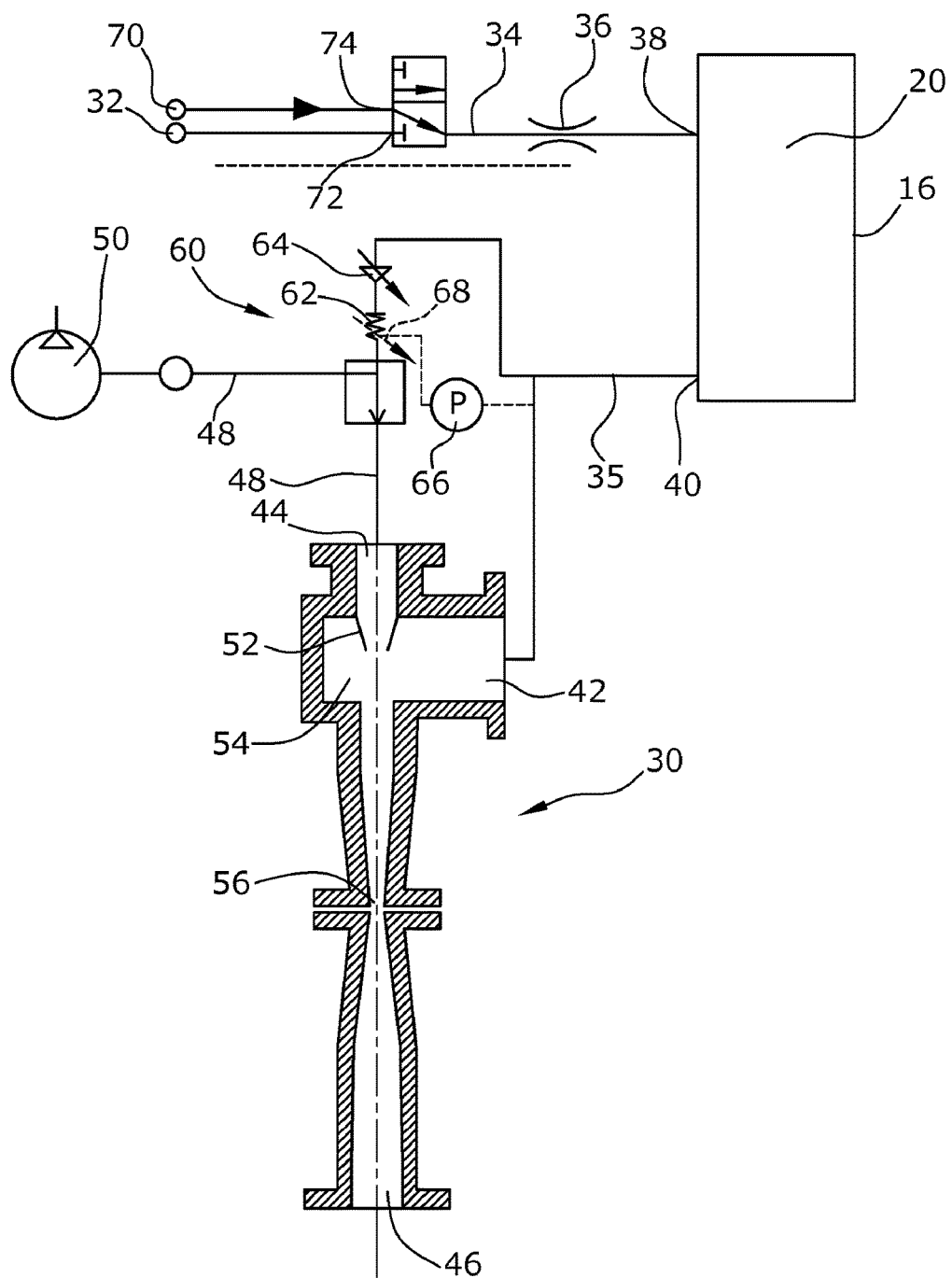
FIG. 2 shows an enlarged schematic diagram of the sample gas flow illustrating a suction jet pump.

An alternative embodiment is illustrated in FIG. 2 by dotted lines. In this embodiment, a pressure sensor 66 is arranged in the second part of the feed line 35, which pressure sensor 66 measures the pressure in the second part of the feed line 35 and is electrically connected with a control unit 68 of the regulating valve 60 which, in the present case, is configured as a pure electromagnetic valve, for example, so that the current feed is adjusted according to the pressure values of the pressure sensor 66. For example, at an excessive absolute pressure in the second part of the feed line 35 and thus too low a negative pressure, the current feed is enhanced by corresponding signals of the control unit 68 for further opening the valve cross-section of the regulating valve 60, whereby the propellant gas flow is increased and thus the negative pressure in the second part of the feed line 35 is enhanced.

The pressure in the second part of the feed line 35 and thus in the analysis cell 16 is regulated in both embodiments by a change of the propellant gas pressure. Only the amount of propellant gas required for the desired volume flow is thereby necessary. The propellant gas flow and thus the propellant pressure in the propellant gas line 48 of the suction jet pump 30 are accordingly always regulated as a direct function of the sample gas flow and/or the feed pressure in the analysis cell 16 and/or the second part of the feed line 35.

Besides this feeding of a sample gas flow via the sample gas connection 32, the device offers the possibility to suck in a purging gas flow or reference gas flow via a reference or purging gas connection 70. For this purpose, a branch 72 is defined in the first part of the feed line 34 upstream of the analysis cell 16 and upstream of the nozzle 36, in which branch a switch valve 74 is arranged by which the sample gas flow can be interrupted and a connection with the reference or purging gas connection 70 can be established. Via this connection, either a reference gas for calibrating the detector 22 can be sucked into the analysis cell 16 or a purging gas for removing impurities which were introduced during previous measurements, so that, after purging, the switch valve 74 is operated to close the purging gas connection 70 and to subsequently clear the first part of the feed line 34 for the sample gas flow. This purging gas should if possible not contain any molecules which are to be measured in the sample gas flow during the subsequent measurements so that a falsification of the measuring results by residues of the purging gas in the analysis cell is avoided.

Such a device for determining the concentration of a least one gas in a sample gas flow by infrared absorption spectroscopy is inexpensive to manufacture and can be operated in an almost maintenance-free manner. The attainable measuring results are very exact and reproducible, in particular due to the reliable avoidance of pressure surges. The consumption of propellant gas is also reduced so that costs are saved. The device is further insensitive to condensate precipitation and can be operated at high temperatures of more than 50° C. ambient temperature. The sample gas may have temperatures of 200° C. A broad band power pack can be used for voltage supply purposes. The current consumption is low since the vacuum pump does not require any voltage supply.

It should be appreciated that the present invention is not limited to the described exemplary embodiment but that various modifications are possible; reference should be had to the appended claims.

What is claimed is:

1. A device for determining a concentration of at least one gas in a sample gas flow by infrared absorption spectroscopy, the device comprising:
   an infrared radiation source configured to emit a radiation which is conducted through an analysis cell;
   a feed line;
   the sample gas flow which is configured to be conducted into and out of the analysis cell via the feed line;
   a detector configured to measure an absorption spectrum arising in the analysis cell;
   a suction jet pump comprising a propellant gas connection, the suction jet pump being arranged downstream of the analysis cell and being configured to feed the sample gas flow through the analysis cell via the feed line; and
   a propellant gas line extending to the propellant gas connection of the suction jet pump, the propellant gas line comprising a regulating valve which is configured to regulate a propellant pressure in the propellant gas line,
   wherein,
   the regulating valve is a proportional valve which is configured to regulate the propellant pressure in the propellant gas line based exclusively on a direct function of a feed pressure in the feed line downstream of the analysis cell or of a pressure in the analysis cell so that a higher propellant pressure is generated in the propellant gas line based on a decreasing negative pressure in the feed line.

2. The device as recited in claim 1, wherein the proportional valve is a pneumatic valve comprising a control chamber which is fluidically connected with the feed line.

3. The device as recited in claim 2, further comprising a pressure sensor arranged downstream of the analysis cell in the feed line or in the analysis cell.

4. The device as recited in claim 3, wherein,
   the regulating valve comprises a control unit, and
   the pressure sensor is connected with the control unit of the regulating valve, the pressure sensor being configured to regulate an opening position of the regulating valve as a function of pressure values measured by the pressure sensor.

5. The device as recited in claim 1, further comprising:
   a sample gas connection; and
   a reference or purging gas connection which is configured to be selectively connectable with the feed line upstream of the analysis cell.

6. The device as recited in claim 5, further comprising:
   a branch arranged in the feed line; and
   a switch valve arranged in the branch, the switch valve being configured to fluidically connect the feed line with the sample gas connection or with the reference or purging gas connection.

7. The device as recited in claim 1, further comprising a nozzle arranged in the feed line upstream of the analysis cell.

8. The device as recited in claim 1, wherein, the infrared radiation source is a quantum cascade laser.

9. A method for determining a concentration of at least one gas in a sample gas flow by infrared absorption spectroscopy with the device as recited in claim 4, the method comprising:
- providing the device as recited in claim 4 further comprising a computing unit configured to determine the concentration of the at least one gas in the sample gas flow;
- feeding the sample gas flow into the analysis cell via the feed line using the suction jet pump;
- conducting the radiation from the infrared radiation source into the analysis cell;
- determining an absorption spectrum of the radiation exiting the analysis cell with the detector;
- determining the concentration of the at least one gas in the sample gas flow via the computing unit based on the absorption spectrum;

wherein,
the suction jet pump comprises a propelling nozzle, and
the propellant pressure in the propellant gas line and the propelling nozzle of the suction jet pump are each regulated as a direct function of a feed pressure in the analysis cell or in the feed line.

10. The method as recited in claim 9, wherein a higher propellant pressure is generated in the propellant gas line as a negative pressure in the feed line is reduced.

11. The method as recited in claim 9, further comprising:
- directing the feed pressure in the feed line into the control chamber of the proportional valve in the propellant gas line.

12. The method as recited in claim 9, further comprising:
- measuring the feed pressure in the feed line so as to obtain measured values; and
- providing the measured values to the control unit of the regulating valve arranged in the propellant gas line.

* * * * *